(12) United States Patent
Zones et al.

(10) Patent No.: US 10,589,260 B2
(45) Date of Patent: Mar. 17, 2020

(54) MOLECULAR SIEVE SSZ-110, ITS SYNTHESIS AND USE

(71) Applicant: Chevron U.S.A. Inc., San Ramon, CA (US)

(72) Inventors: Stacey Ian Zones, San Francisco, CA (US); Tracy Margaret Davis, Novato, CA (US); Dan Xie, Richmond, CA (US); Cong-Yan Chen, Kensington, CA (US); Howard Steven Lacheen, Richmond, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 16/252,779

(22) Filed: Jan. 21, 2019

(65) Prior Publication Data
US 2019/0224655 A1    Jul. 25, 2019

Related U.S. Application Data

(60) Provisional application No. 62/621,116, filed on Jan. 24, 2018.

(51) Int. Cl.
*C01B 39/48* (2006.01)
*B01J 20/18* (2006.01)
(Continued)

(52) U.S. Cl.
CPC ............ *B01J 29/70* (2013.01); *B01J 20/18* (2013.01); *B01J 20/28061* (2013.01); *B01J 20/28071* (2013.01); *B01J 20/3057* (2013.01); *B01J 20/3085* (2013.01); *B01J 35/1019* (2013.01); *B01J 35/1038* (2013.01);
(Continued)

(58) Field of Classification Search
CPC ....... C01B 39/48; C01P 2002/72; B01J 20/18; B01J 29/70; C07C 2529/70; C07C 5/2708
See application file for complete search history.

(56) References Cited

U.S. PATENT DOCUMENTS

| | | | |
|---|---|---|---|
| 9,601,197 B2 * | 3/2017 | Nango | G11C 5/148 |
| 9,604,197 B2 | 3/2017 | Schmidt et al. | |
| 2018/0093255 A1 * | 4/2018 | Chen | B01D 53/9418 |

FOREIGN PATENT DOCUMENTS

WO    2007065794    6/2007

OTHER PUBLICATIONS

Brand et al, "Enantiomerically enriched .. polycrystalline molecular sieves", PNAS May 16, 2017, (114) 20 5101-5106 (Year: 2017).*

(Continued)

*Primary Examiner* — David M Brunsman
(74) *Attorney, Agent, or Firm* — Terrence M. Flaherty

(57) ABSTRACT

An aluminosilicate molecular sieve of STW framework type, designated herein as SSZ-110, and having a molar ratio of $SiO_2/Al_2O_3$ of less than 100, is provided. SSZ-110 may be synthesized using an organic structure directing agent selected from one or more of 1,4-bis(2,3-dimethyl-1H-imidazolium)butane dications, 1,5-bis(2,3-dimethyl-1H-imidazolium)pentane dications, and 1,6-bis(2,3-dimethyl-1H-imidazolium)hexane dications. SSZ-110 may be used in organic compound conversion reactions and sorptive processes.

10 Claims, 1 Drawing Sheet

(51) Int. Cl.
  B01J 29/70 (2006.01)
  B01J 20/30 (2006.01)
  B01J 37/00 (2006.01)
  B01J 37/03 (2006.01)
  B01J 35/10 (2006.01)
  B01J 20/28 (2006.01)
  C07C 5/27 (2006.01)
(52) U.S. Cl.
  CPC ......... B01J 37/0018 (2013.01); B01J 37/031 (2013.01); C01B 39/48 (2013.01); C07C 5/2708 (2013.01); *C01P 2002/72* (2013.01); *C07C 2529/70* (2013.01)

(56) References Cited

OTHER PUBLICATIONS

Lu et al, "Synthesis of STW zeolites using imidazolium-based diactions of varying length", J. Mater. Chem. A 2018 (6) 1485 (Year: 2018).*

Schmidt et al, "CIT-7, a crystalline molecular sieve with pores bounded by 8 and 10-member rings", Chem SCi 2015 (6) 1758 (Year : 2015).*

Vinaches et al, "Introduction of Al into the HPM-1 framework by in situ generated seeds as an alternative methodology", Appl. Sci 2018 (8) 1634 (Year: 2018).*

Brand et al, "Enantiomerically enriched ,. polycrystalline molecular sieves", supplementary materials PNAS May 16, 2017, (114) 20 5101-5106 (Year: 2017).*

PCT International Search Report, International Application No. PCT/IB2019/050472, dated May 6, 2019.

P. Lu, L. Gomez-Hortiguela, L. Xu and M.A. Camblor "Synthesis of STW zeolites using imidazolium-based dications of varying length" J. Mater. Chem. A 2018, 6, 1485-1495.

A. Rojas, O. Arteaga, B. Kahr and M.A. Camblor "Synthesis, Structure, and Optical Activity of HPM-1, a Pure Silica Chiral Zeolite" J. Am. Chem. Soc. 2013, 135, 11975-11984.

L. Tang, L. Shi, C. Bonneau, J. Sun, H. Yue, A. Ojuva, B-L. Lee, M. Kritikos, R.G. Bell, Z. Bacsik, J. Mink and X. Zou "A zeolite family with chiral and achiral structures built from the same building layer" Nature Mater. 2008, 7, 381-385.

A. Rojas and M.A. Camblor "A Pure Silica Chiral Polymorph with Helical Pores" Angew. Chem. Int. Ed. 2012, 51, 3854-3856.

N. Zhang, L. Shi, T. Yu, T. Li, W. Hua and C. Lin "Synthesis and characterization of pure STW-zeotype germanosilicate, Cu- and Co-substituted STW-zeotype materials" J. Solid State Chem. 2015, 225, 271-277.

L. Shi, T. Yu, S. Lin, Y. Yuan, J. Wang and N. Zhang "Synthesis and Characterization of B-Substituted High-siliceous STW-type Silicate Zeolite" Chem. J. Chinese U. 2015, 36, 1467-1471.

S.K. Brand, J.E. Schmidt, M.W. Deem, E Daeyaert, Y. Ma, O. Terasaki, M. Orazov and M.E. Davis "Enantiomerically enriched, polycrystalline molecular sieves" PNAS 2017, 114, 5101-5106.

* cited by examiner

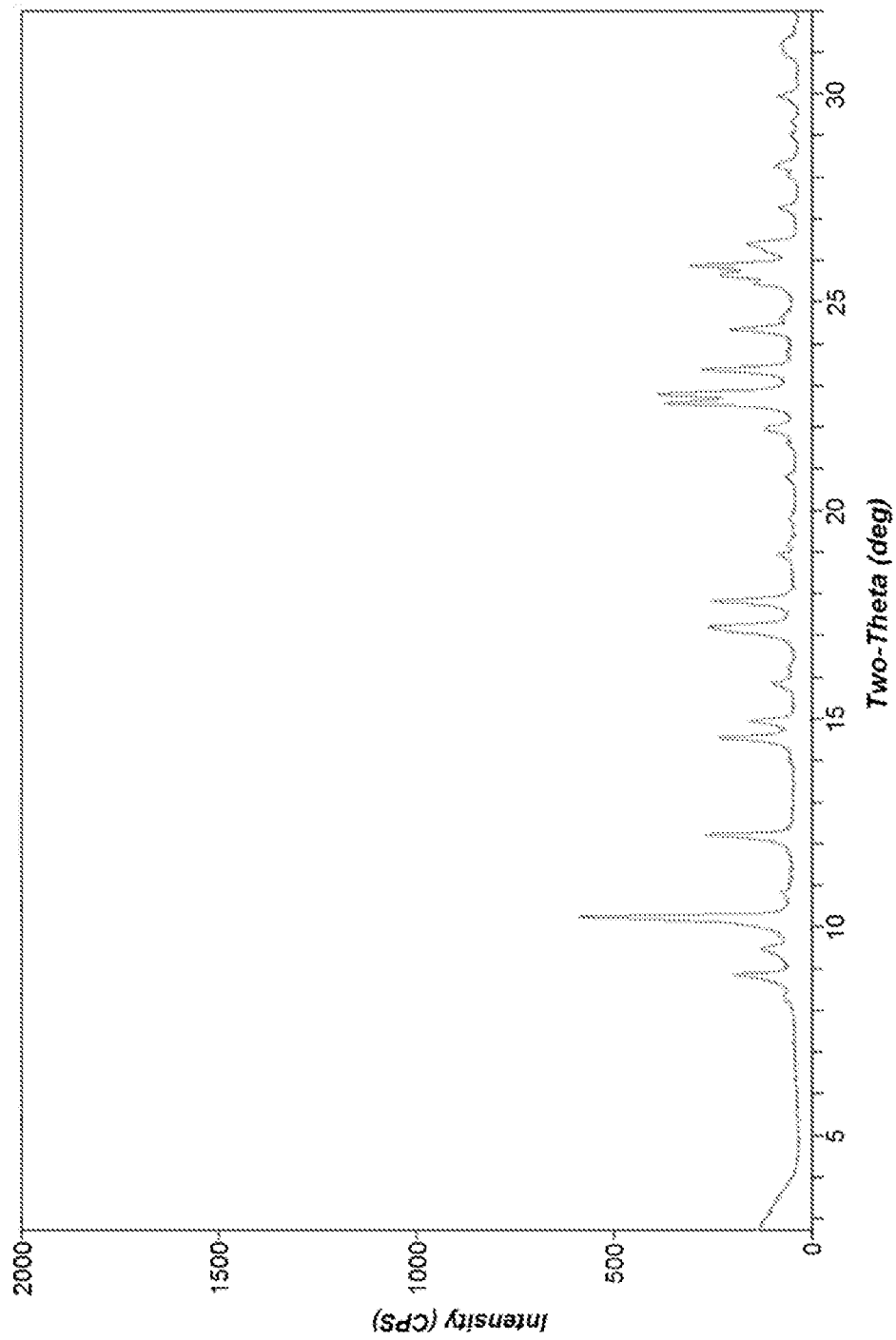

MOLECULAR SIEVE SSZ-110, ITS SYNTHESIS AND USE

CROSS-REFERENCE TO RELATED APPLICATIONS

This application claims priority to and the benefit of U.S. Provisional Application Ser. No. 62/621,116, filed Jan. 24, 2018.

FIELD

The present disclosure relates to a novel synthetic aluminosilicate molecular sieve of STW framework type, designated as SSZ-110, its synthesis and its use in organic compound conversion reactions and sorptive processes.

BACKGROUND

Zeolitic materials are known to have utility as sorbent materials and to have catalytic properties for various types of organic conversion reactions. Certain zeolitic materials are ordered, porous crystalline materials having a definite crystalline structure as determined by X-ray diffraction. Within the zeolitic material, there are a large number of smaller cavities which may be interconnected by a number of still smaller channels or pores. Since the dimensions of these pores are such as to accept for sorption molecules of certain dimensions while rejecting those of larger dimensions, these materials have come to be known as "molecular sieves" and are utilized in a variety of ways to take advantage of these properties.

Molecular sieves are classified by the Structure Commission of the International Zeolite Association according to the rules of the IUPAC Commission on Zeolite Nomenclature. According to this classification, framework-type zeolites and other crystalline microporous molecular sieves, for which a structure has been established, are assigned a three-letter code and are described in the "*Atlas of Zeolite Framework Types,*" Sixth Revised Edition, Elsevier (2007).

Molecular sieves identified by the International Zeolite Association as having the framework type STW are known. Germanosilicate zeolite SU-32 is a known crystalline STW material synthesized using diisopropylamine as a structure directing agent (see, L. Tang et al., *Nature Mater.* 2008, 7, 381-385). SU-32 contains 10-membered ring chiral helical channels which are intersected at different levels by straight 8-membered ring channels.

A. Rojas et al. (*Angew. Chem. Int. Ed.* 2012, 51, 3854-3856) disclose a pure-silica chiral zeolite of STW framework type, HPM-1, and its synthesis using 2-ethyl-1,3,4-trimethylimidazolium cations as a structure directing agent.

N. Zhang et al. (*J. Solid State Chem.* 2015, 225, 271-277) disclose the synthesis of pure STW-type germanosilicate and Cu- and Co-substituted STW-zeotype materials using N,N-diethylethylenediamine as a structure directing agent.

L. Shi et al. (*Chem. J. Chinese U.* 2015, 36, 1467-1471) disclose the synthesis of a boron-substituted STW-type silicate zeolite using 2-ethyl-1,3,4-trimethylimidazolium cations as a structure directing agent.

U.S. Pat. No. 9,604,197 discloses the synthesis of a molecular sieve of STW framework type using 1,2,3,4,5-pentamethyl-1H-imidazol-3-ium cations as a structure directing agent. Aluminosilicate STW materials are reported to have a molar ratio of silicon to aluminum of at least 100.

P. Lu et al. (*J. Mater. Chem. A* 2018, 1485-1495) disclose the synthesis of germanosilicate and pure silica STW-type zeolites using imidazolium-based dications of varying length.

For catalytic applications, incorporation of catalytic active sites, such as aluminum atoms, is important to impart acidic properties to the molecular sieve.

Accordingly, a new aluminosilicate molecular sieve of STW framework type, designated herein as SSZ-110, having a $SiO_2/Al_2O_3$ molar ratio of less than 100, is provided. Molecular sieve SSZ-110 may be synthesized using the organic structure directing agents disclosed herein.

SUMMARY

In one aspect, there is provided a novel aluminosilicate molecular sieve of STW framework type having a molar ratio of $SiO_2/Al_2O_3$ of less than 100.

In another aspect, there is provided a method of synthesizing an aluminosilicate molecular sieve of STW framework type, the method comprising: (a) providing a reaction mixture comprising: (1) a source of silicon oxide; (2) a source of aluminum oxide; (3) an organic structure directing agent (Q) comprising one or more of 1,4-bis(2,3-dimethyl-1H-imidazolium)butane dications, 1,5-bis(2,3-dimethyl-1H-imidazolium)pentane dications, and 1,6-bis(2,3-dimethyl-1H-imidazolium)hexane dications; (4) a source of fluoride ions; and (5) water; and (b) subjecting the reaction mixture to crystallization conditions sufficient to form crystals of the aluminosilicate molecular sieve.

In a further aspect, there is provided an aluminosilicate molecular sieve of STW framework type and, in its as-synthesized form, comprising one or more of 1,4-bis(2,3-dimethyl-1H-imidazolium)butane dications, 1,5-bis(2,3-dimethyl-1H-imidazolium)pentane dications, and 1,6-bis(2,3-dimethyl-1H-imidazolium)hexane dications in its pores.

In yet a further aspect, there is provided a process for converting a feedstock comprising an organic compound to a conversion product which comprises contacting the feedstock at organic compound conversion conditions with a catalyst comprising an active form of the aluminosilicate molecular sieve described herein.

BRIEF DESCRIPTION OF THE DRAWINGS

FIG. 1 is a powder X-ray diffraction (XRD) pattern of the as-synthesized molecular sieve prepared in Example 2.

DETAILED DESCRIPTION

Introduction

The term "aluminosilicate" refers to a molecular sieve composition including silicon and aluminum oxides within its framework. In some cases, either of these oxides may be optionally substituted with other oxides. "Pure aluminosilicates" are those molecular sieve structures having no detectable other metal oxides in the framework. When described as "optionally substituted," the respective framework may contain boron, gallium, indium, germanium, tin, titanium, iron, or other atoms substituted for one or more of the atoms not already contained in the parent framework.

The term "framework type" is used in the sense described in the "*Atlas of Zeolite Framework Types,*" Sixth Revised Edition, Elsevier (2007).

The term "as-synthesized" is employed herein to refer to a molecular sieve in its form after crystallization, prior to removal of the organic structure directing agent.

The term "anhydrous" is employed herein to refer to a molecular sieve substantially devoid of both physically adsorbed and chemically adsorbed water.

As used herein, the numbering scheme for the Periodic Table Groups is as disclosed in *Chem. Eng. News* 1985, 63(5), 26-27.

$SiO_2/Al_2O_3$ molar ratio (SAR) is herein determined by Inductively Coupled Plasma-Mass Spectrometry (ICP-MS).

"Surface area" is determined herein by $N_2$ adsorption at its boiling temperature. The B.E.T. surface area is calculated by the 5-point method at $P/P_0$=0.050, 0.088, 0.125, 0.163, and 0.200. Samples are first pre-treated at 400° C. for 6 hours in the presence of flowing, dry $N_2$ so as to eliminate any adsorbed volatiles like water or organics.

"Micropore volume" is determined herein by $N_2$ adsorption at its boiling temperature. Micropore volume is calculated by the t-plot method at $P/P_0$=0.050, 0.088, 0.125, 0.163, and 0.200. Samples are first pre-treated at 400° C. for 6 hours in the presence of flowing, dry $N_2$ so as to eliminate any adsorbed volatiles like water or organics.

"Brønsted acidity" is determined herein by isopropylamine-temperature-programmed desorption (IPam TPD) adapted from the published descriptions by T. J. Gricus Kofke et al. (*J. Catal.* 1988, 114, 34-45), T. J. Gricus Kofke et al. (*J. Catal.* 1989, 115, 265-272), and J. G. Tittensor et al. (*J. Catal.* 1992, 138, 714-720). A sample was pre-treated at 400° C.-500° C. for 1 hour in flowing dry $H_2$. The dehydrated sample was then cooled down to 120° C. in flowing dry helium and held at 120° C. for 30 minutes in a flowing helium saturated with isopropylamine for adsorption. The isopropylamine-saturated sample was then heated up to 500° C. at a rate of 10° C./minute in flowing dry helium. The Brønsted acidity was calculated based on the weight loss vs. temperature by thermogravimetric analysis (TGA) and effluent $NH_3$ and propene by mass spectrometry.

"Constraint Index" (CI) is determined herein according the method described by S. I. Zones et al. (*Micropor. Mesopor. Mater.* 2000, 35-36, 31-46). The test is designed to allow discrimination between pore systems composed of 8, 10 and ≥12 membered ring (MR, the number of tetrahedral or oxygen atoms that make up the ring) pores. The CI value decreases with the increasing pore size of molecular sieves. For example, zeolites are often classified based on the CI values as follows: CI<1 for large pore (12-MR) or extra-large pore (14-MR) molecular sieves; 1≤CI≤12 for medium pore (10-MR) molecular sieves; CI>12 for small pore (8-MR) molecular sieves.

Reaction Mixture

In general, an aluminosilicate molecular sieve of STW framework type may be synthesized by: (a) providing a reaction mixture comprising: (1) a source of silicon oxide; (2) a source of aluminum oxide; (3) an organic structure directing agent (Q) comprising one or more of 1,4-bis(2,3-dimethyl-1H-imidazolium)butane dications, 1,5-bis(2,3-dimethyl-1H-imidazolium)pentane dications, and 1,6-bis(2,3-dimethyl-1H-imidazolium)hexane dications; (4) a source of fluoride ions; and (5) water; and (b) subjecting the reaction mixture to crystallization conditions sufficient to form crystals of the aluminosilicate molecular sieve.

The reaction mixture may have a composition, in terms of molar ratios, within the following ranges set forth in Table 1:

TABLE 1

| Reactants | Useful | Exemplary |
|---|---|---|
| $SiO_2/Al_2O_3$ | 20 to <100 | 20 to 80 |
| $Q/SiO_2$ | 0.20 to 0.75 | 0.25 to 0.65 |
| $F/SiO_2$ | 0.20 to 0.75 | 0.25 to 0.65 |
| $H_2O/SiO_2$ | 2 to 100 | 4 to 40 | wherein Q is as described herein above.

Suitable sources of silicon oxide include colloidal silicas, fumed silicas, precipitated silicas, alkali metal silicates, and tetraalkyl orthosilicates.

Suitable sources of aluminum oxide include hydrated alumina and water-soluble aluminum salts (e.g., aluminum nitrate).

Combined sources of silicon oxide and aluminum oxide can additionally or alternatively be used and can include aluminosilicate zeolites (e.g., zeolite Y) and clays or treated clays (e.g., metakaolin).

Suitable sources of fluoride ions include hydrofluoric acid, ammonium fluoride, and ammonium hydrogen difluoride.

The organic structure directing agent (Q) comprises one or more of 1,4-bis(2,3-dimethyl-1H-imidazolium)butane dications, 1,5-bis(2,3-dimethyl-1H-imidazolium)pentane dications, and 1,6-bis(2,3-dimethyl-1H-imidazolium)hexane dications, represented by the following structures (1) to (3), respectively:

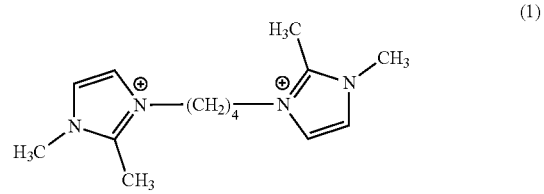

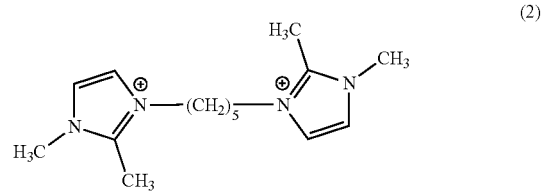

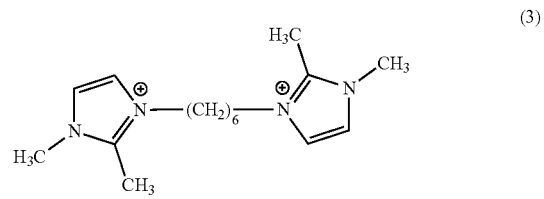

Suitable sources of Q are the hydroxides and/or other salts of the relevant diquaternary ammonium compounds.

The reaction mixture may also contain seeds of a molecular sieve material, such as SSZ-110 from a previous synthesis, desirably in an amount of from 0.01 to 10,000 ppm by weight (e.g., from 100 to 5000 ppm by weight) of the reaction mixture. Seeding can be advantageous in decreasing the amount of time necessary for complete crystallization to occur. In addition, seeding can lead to an increased purity of the product obtained by promoting the nucleation and/or formation of SSZ-110 over any undesired phases.

For each embodiment described herein, the reaction mixture can be supplied by more than one source. Also, two or more reaction components can be provided by one source.

The reaction mixture can be prepared either batch wise or continuously. Crystal size, morphology and crystallization time of the molecular sieve herein can vary with the nature of the reaction mixture and the crystallization conditions.

Crystallization and Post-Synthesis Treatment

Crystallization of the molecular sieve from the above reaction mixture can be carried out under either static, tumbled or stirred conditions in a suitable reactor vessel, such as polypropylene jars or Teflon-lined or stainless-steel autoclaves, at a temperature of from 125° C. to 200° C. for a time sufficient for crystallization to occur at the temperature used, e.g., from 5 to 40 days. Crystallization is usually carried out in an autoclave so that the reaction mixture is subject to autogenous pressure.

Once the molecular sieve crystals have formed, the solid product is recovered from the reaction mixture by standard mechanical separation techniques such as centrifugation or filtration. The recovered crystals are water-washed and then dried to obtain the as-synthesized molecular sieve crystals. The drying step is typically performed at a temperature of less than 200° C.

As a result of the crystallization process, the recovered crystalline product contains within its pore structure at least a portion of the organic structure directing agent used in the synthesis.

In its as-synthesized and anhydrous form, molecular sieve SSZ-110 can have a chemical composition comprising the following molar relationship set forth in Table 2:

TABLE 2

|  | Broadest | Exemplary |
| --- | --- | --- |
| $SiO_2/Al_2O_3$ | <100 | 20 to 80 |
| $Q/SiO_2$ | >0 to 0.1 | >0 to 0.1 |
| $F/SiO_2$ | >0 to 0.1 | >0 to 0.1 | wherein Q is as described herein above.

The Q and F components, which are associated with the as-synthesized material as a result of their presence during crystallization, are easily removed by conventional post-crystallization methods.

The as-synthesized molecular sieve may be subjected to treatment to remove part or all of the organic structure directing agent used in its synthesis. This can be conveniently effected by thermal treatment in which the as-synthesized material is heated at a temperature of at least about 370° C. for at least 1 minute and generally not longer than 20 hours. The thermal treatment can be performed at a temperature up to 925° C. While sub-atmospheric pressure can be employed for the thermal treatment, atmospheric pressure is desired for reasons of convenience. Additionally or alternatively, the organic structure directing agent can be removed by treatment with ozone (see, e.g., A. N. Parikh et al., *Micropor. Mesopor. Mater.* 2004, 76, 17-22). The organic-depleted product, especially in its metal, hydrogen and ammonium forms, is particularly useful in the catalysis of certain organic (e.g., hydrocarbon) conversion reactions. In the present disclosure, the organic-depleted molecular sieve in its hydrogen form is referred to as "active form" of the molecular sieve, with or without metal function present.

The synthesis of the present molecular sieve can be accomplished in the absence of Group 1 or 2 metal cations, thereby obviating the need for ion exchange of the product after treatment to remove any occluded organic structure directing agent. However, depending on the $SiO_2/Al_2O_3$ molar ratio of the material, any cations in the molecular sieve can be replaced in accordance with techniques well known in the art (e.g., by ion exchange with other cations). Preferred replacing cations can include metal ions, hydrogen ions, hydrogen precursor (e.g., ammonium) ions, and mixtures thereof. Particularly preferred replacing cations can include those that tailor the catalytic activity for certain organic compound conversion reactions (e.g., hydrogen, rare earth metals, and/or one or more metals of Groups 2-15 of the Periodic Table of Elements).

In its calcined form, molecular sieve SSZ-110 can have a chemical composition comprising the following molar relationship:

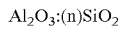

$Al_2O_3:(n)SiO_2$ wherein n is <100 (e.g., 20 to <100, 20 to 95, 20 to 90, 20 to 85, 20 to 80, 20 to 75, 20 to 70, 20 to 65, 20 to 60, 25 to <100, 25 to 95, 25 to 90, 25 to 85, 25 to 80, 25 to 75, 25 to 70, 25 to 65, 25 to 60, 30 to <100, 30 to 95, 30 to 90, 30 to 85, 30 to 80, 30 to 75, 30 to 70, 30 to 65, 30 to 60, 35 to <100, 35 to 95, 35 to 90, 35 to 85, 35 to 80, 35 to 75, 35 to 70, 35 to 65, 35 to 60, 40 to <100, 40 to 95, 40 to 90, 40 to 85, 40 to 80, 40 to 75, 40 to 70, 40 to 65, or 40 to 60).

Sorption and Catalysis

Molecular sieve SSZ-110 may be used as a sorbent or as a catalyst to catalyze a wide variety of organic compound conversion processes including many of present commercial/industrial importance. Examples of chemical conversion processes which are effectively catalyzed by SSZ-110, by itself or in combination with one or more other catalytically active substances including other crystalline catalysts, include those requiring a catalyst with acid activity. Examples of organic conversion processes which may be catalyzed by SSZ-110 include alkylation, (hydro)cracking, disproportionation, isomerization, and oligomerization. Other organic conversion processes may include the reaction of alcohols with olefins and the conversion of organic oxygenates to hydrocarbons.

As in the case of many catalysts used in organic compound (e.g., hydrocarbon) conversion processes, it may be desirable to incorporate SSZ-110 with another material resistant to the temperatures and other conditions employed in organic conversion processes. Such materials can include active and inactive materials and synthetic or naturally occurring zeolites, as well as inorganic materials such as clays, silica, and/or metal oxides such as alumina. The latter may be either naturally occurring or in the form of gelatinous precipitates or gels, including mixtures of silica and metal oxides. Use of a material in conjunction with the present molecular sieve, i.e., combined therewith and/or present during synthesis of the molecular sieve, which is active, can tend to change the conversion and/or selectivity of the catalyst in certain organic conversion processes. Inactive materials can suitably serve as diluents to control the amount of conversion in a given process so that products can be obtained in an economic and orderly manner without employing other (costlier) means for controlling the rate of reaction. These materials may be incorporated into naturally occurring clays (e.g., bentonite and kaolin) to improve the crush strength of the catalyst under commercial operating conditions. These materials (i.e., clays, oxides, etc.) can function as binders for the catalyst. It can be desirable to provide a catalyst having good crush strength, because in commercial use it can be desirable to prevent the catalyst from breaking down into powder-like materials (attrition). These clay and/or oxide binders have been employed normally only for the purpose of improving the crush strength of the catalyst.

Naturally occurring clays which can be composited with the SSZ-110 can include the montmorillonite and kaolin family, which families include the sub-bentonites, and the kaolins commonly known as Dixie, McNamee, Georgia, and Florida clays, or others in which the main mineral constituent is halloysite, kaolinite, dickite, nacrite, or anauxite. Such clays can be used in the raw state as originally mined or initially subjected to calcination, acid treatment, or chemical modification. Binders useful for compositing with the present molecular sieve can additionally or alternatively include inorganic oxides, such as silica, zirconia, titania, magnesia, beryllia, alumina, and mixtures thereof.

Alternatively or in addition to the foregoing materials, SSZ-110 can be composited with a porous matrix material such as silica-alumina, silica-magnesia, silica-zirconia, silica-thoria, silica-beryllia, silica-titania, and/or one or more ternary compositions such as silica-alumina-thoria, silica-alumina-zirconia silica-alumina-magnesia, and silica-magnesia-zirconia.

The relative proportions of molecular sieve SSZ-110 and inorganic oxide matrix may vary widely, with the SSZ-110 content ranging from 1 to 90 wt. % (e.g., 2 to 80 wt. %) of the composite.

EXAMPLES

The following illustrative examples are intended to be non-limiting.

Example 1

A tared Teflon cup was charged with 1,1'-(1,4-butanediyl)bis[2,3-dimethyl-1H-imidazolium] dihydroxide (2.5 mmoles of hydroxide equivalents). Then, 1.04 grams of tetraethyl orthosilicate (5 mmoles of $SiO_2$) and 0.02 grams of Reheis F-2000 as an alumina source were added to provide a starting $SiO_2/Al_2O_3$ molar ratio of 50. Seeds of SSZ-110 (10 mg) from a previous synthesis were then added to the mixture. The Teflon cup was kept closed for 2 days and then the cup was opened to start the evaporation of some water and the ethanol from tetraethyl orthosilicate. When the solids content was found to be 1.09 grams, then a 50% HF solution (0.09 grams) was added to the reaction mixture. The Teflon cup was capped and placed within a Parr steel autoclave reactor. The autoclave was placed in an oven and heated at 170° C. with rotation (43 rpm) for 2 weeks. The solid products were recovered from the cooled reactor by filtration, washed with deionized water and dried at 95° C.

Powder XRD of the as-synthesized product was consistent with the material being a molecular sieve of STW topology.

Chemical analysis shows that the as-synthesized product had an aluminum content of 1.6 wt.%, a fluoride content of 0.47 wt. %, and a $SiO_2/Al_2O_3$ molar ratio of 49.

Example 2

A tared Teflon liner was charged with 0.90 g of CBV-780 Y-zeolite powder (Zeolyst International; $SiO_2/Al_2O_3$ molar ratio=80) and 7.5 mmole of 1,1'-(1,4-butanediyl)bis[2,3-dimethyl-1H-imidazolium] dihydroxide. The mixture was placed in a fume hood and the water content was reduced by evaporation over several days to achieve a target $H_2O/SiO_2$ molar ratio of 7. Then, 7.5 mmole of a 50% HF solution was added in dropwise. The liner was capped and placed within a Parr steel autoclave reactor. The autoclave was placed in an oven and heated at 160° C. with rotation (43 rpm) for 7 days. The solid products were recovered from the cooled reactor by filtration, washed with deionized water and dried at 95° C.

The resulting as-synthesized product was analyzed by powder XRD. The powder X-ray diffraction pattern in FIG. 1 is consistent with the product being a molecular sieve of STW framework type.

The as-synthesized molecular sieve product of Example 2 was calcined inside a muffle furnace under a flow of 2% oxygen/98% nitrogen heated to 595° C. at a rate of 1° C./minute and held at 595° C. for five hours and cooled to ambient temperature.

The powder XRD pattern indicated that the material remains stable after calcination to remove the structure directing agent.

The physical properties of the calcined molecular sieve are summarized in Table 3.

TABLE 3

| | |
|---|---|
| Micropore Volume | 0.0829 $cm^3/g$ |
| B.E.T. Surface Area | 206.48 $m^2/g$ |
| Brønsted Acidity | 279 µmol/g |

Example 4

Constraint Index Determination

The calcined molecular sieve of Example 2 was pelletized at 4-5 kpsi and crushed and meshed to 20-40. Then, 0.50 g of molecular sieve was packed into a ⅜ inch stainless steel tube with alundum on both sides of the molecular sieve bed. A Lindburg furnace was used to heat the reactor tube. Helium was introduced into the reactor tube at 10 mL/min and at atmospheric pressure. The reactor was heated to about 371° C. and a 50/50 (w/w) feed of n-hexane and 3-methylpentane was introduced into the reactor at a rate of 8 µL/min. Feed delivery was made via a Brownlee pump. Direct sampling into a gas chromatograph (GC) began after 15 minutes of feed introduction.

The Constraint Index value (not including 2-methylpentane) was calculated from the GC data using methods known in the art and was found to be between 2.25 and 2.96 for times on stream from 15 to 225 minutes, which is characteristic for 10-membered ring molecular sieves.

The invention claimed is:

1. A method of synthesizing an aluminosilicate molecular sieve of STW framework type, the method comprising:
    (a) providing a reaction mixture comprising:
        (1) a source of silicon oxide;
        (2) a source of aluminum oxide;
        (3) an organic structure directing agent (Q) comprising one or more of 1,4-bis(2,3-dimethyl-1H-imidazolium)butane dications, 1,5-bis(2,3-dimethyl-1H-imidazolium)pentane dications, and 1,6-bis(2,3-dimethyl-1H-imidazolium)hexane dications;
        (4) a source of fluoride ions;
        (5) water; and
    (b) subjecting the reaction mixture to crystallization conditions sufficient to form crystals of the molecular sieve.

2. The method of claim 1, wherein the reaction mixture has a composition, in terms of molar ratios, as follows:

| | |
|---|---|
| $SiO_2/Al_2O_3$ | 20 to <100 |
| $Q/SiO_2$ | 0.20 to 0.75 |
| $F/SiO_2$ | 0.20 to 0.75 |
| $H_2O/SiO_2$ | 2 to 100. |

3. The method of claim 1, wherein the reaction mixture has a composition, in terms of molar ratios, as follows:

| | |
|---|---|
| $SiO_2/Al_2O_3$ | 20 to 80 |
| $Q/SiO_2$ | 0.25 to 0.65 |
| $F/SiO_2$ | 0.25 to 0.65 |
| $H_2O/SiO_2$ | 4 to 40. |

4. The method of claim 1, wherein the reaction mixture further comprises seeds.

5. The method of claim 4, wherein the seeds are present in an amount of 0.01 to 10,000 ppm by weight of the reaction mixture.

6. The method of claim 4, wherein the seeds comprise a molecular sieve of STW framework type.

7. The method of claim 1, wherein the crystallization conditions include a temperature of from 125° C. to 200° C.

8. An aluminosilicate molecular sieve of STW framework type and, in its as-synthesized form, comprising one or more of 1,4-bis(2,3-dimethyl-1H-imidazolium)butane dications, 1,5-bis(2,3-dimethyl-1H-imidazolium)pentane dications, and 1,6-bis(2,3-dimethyl-1H-imidazolium)hexane dications in its pores.

9. The aluminosilicate molecular sieve of claim 8, and having a molar ratio of $SiO_2/Al_2O_3$ of less than 100.

10. The molecular sieve of claim 9, wherein the molar ratio of $SiO_2/Al_2O_3$ in a range of 20 to 80.

* * * * *